(12) United States Patent
Kim et al.

(10) Patent No.: US 11,831,239 B2
(45) Date of Patent: Nov. 28, 2023

(54) CURRENT STIMULATOR FOR RECORDING CRANIAL NERVE SIGNALS AND OPERATION METHOD OF CURRENT STIMULATOR

(71) Applicant: SAMSUNG ELECTRONICS CO., LTD., Suwon-si (KR)

(72) Inventors: Seong Joong Kim, Hwaseong-si (KR); Chisung Bae, Yongin-si (KR); Hankyu Lee, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 17/873,663

(22) Filed: Jul. 26, 2022

(65) Prior Publication Data
US 2023/0208286 A1    Jun. 29, 2023

(30) Foreign Application Priority Data

Dec. 29, 2021    (KR) .................. 10-2021-0191043

(51) Int. Cl.
*H02M 3/04*    (2006.01)
*H02M 3/07*    (2006.01)
(Continued)

(52) U.S. Cl.
CPC ............... *H02M 3/07* (2013.01); *H03L 7/06* (2013.01); *G11C 27/026* (2013.01)

(58) Field of Classification Search
CPC . H01M 3/04; H01M 3/06; H01M 3/07; H03L 7/06; G05F 3/26; G05F 3/262; G11C 27/026; A61N 1/36; A61N 1/36014; A61N 1/3605; H02M 3/04; H02M 3/06; H02M 3/07

See application file for complete search history.

(56) References Cited

U.S. PATENT DOCUMENTS 9,636,027 B2    5/2017    Choi et al.
10,660,575 B2    5/2020    MacCallum
(Continued)

FOREIGN PATENT DOCUMENTS

WO    WO 2019/010343 A1    1/2019

OTHER PUBLICATIONS

Abbott, Jeffrey, et al. "The design of a CMOS nanoelectrode array with 4096 current-clamp/voltage-clamp amplifiers for intracellular recording/stimulation of mammalian neurons." *IEEE journal of solid-state circuits* vol. 55. Issue 9 (2020). pp 2567-2582.

*Primary Examiner* — Long Nguyen
(74) *Attorney, Agent, or Firm* — NSIP Law

(57) ABSTRACT

A current stimulator includes a first current generation circuit configured to generate a first current, injectable into a cranial nerve cell, through a current mirroring based on a plurality of transistor pairs; and a second current generation circuit, driven by a clock, configured to generate a second current smaller than the first current by controlling a charge rate based on a voltage difference between terminals of a capacitor. A first output impedance of the first current generation circuit and a second output impedance of the second current generation circuit have a magnitude greater than or equal to a predetermined ratio to a load impedance corresponding to the cranial nerve cell.

20 Claims, 12 Drawing Sheets

(51) Int. Cl.
 H03L 7/06 (2006.01)
 G11C 27/02 (2006.01)

(56) References Cited

U.S. PATENT DOCUMENTS

| | | |
|---|---|---|
| 10,903,810 B2 | 1/2021 | Kim |
| 11,592,857 B2 * | 2/2023 | Shen ........................ G05F 3/262 |
| 2019/0091470 A1 | 3/2019 | Lee et al. |
| 2020/0011742 A1 * | 1/2020 | Ma ............................ G05F 3/24 |
| 2021/0244280 A1 | 8/2021 | Blaauw et al. |
| 2022/0414435 A1 | 12/2022 | Lee et al. |

* cited by examiner

Current mirror mode for positive current

CURRENT STIMULATOR FOR RECORDING CRANIAL NERVE SIGNALS AND OPERATION METHOD OF CURRENT STIMULATOR

CROSS-REFERENCE TO RELATED APPLICATIONS

This application claims the benefit under 35 USC § 119(a) of Korean Patent Application No. 10-2021-0191043, filed on Dec. 29, 2021, at the Korean Intellectual Property Office, the entire disclosure of which is incorporated herein by reference for all purposes.

BACKGROUND

1. Field

The following description relates to a current stimulator for recording cranial nerve signals and an operation method of the current stimulator.

2. Description of Related Art

Various methods may be used for analyzing human biosignals. For example, multiple signals of neurons measured by multiple electrodes may be used to analyze a brainwave. In addition, a signal transduction scheme of a brain may be interpreted by passing a current of a predetermined magnitude to a cranial nerve cell and observing an intracellular signal. Therefore, there is a demand for accurately providing a current for stimulating a cranial nerve cell without noise.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a current stimulator includes a first current generation circuit configured to generate a first current, injectable into a cranial nerve cell, through a current mirroring based on a plurality of transistor pairs; and a second current generation circuit, driven by a clock, configured to generate a second current smaller than the first current by controlling a charge rate based on a voltage difference between terminals of a capacitor. A first output impedance of the first current generation circuit and a second output impedance of the second current generation circuit have a magnitude greater than or equal to a predetermined ratio to a load impedance corresponding to the cranial nerve cell.

The second current generation circuit may include a first switch and a second switch configured to operate complementarily based on a switching of the clock; and a capacitor, disposed between the first switch and the second switch, configured to adjust a magnitude of the second current by controlling the charge rate.

The magnitude of the second current may be determined based on any one or any combination of any two or more of a frequency of the clock, a capacitance of the capacitor, and a difference between an input voltage and an output voltage of the second current generation circuit.

The second current generation circuit may be further configured to generate the second current in a second current section in which the magnitude of the second current increases linearly as the frequency of the clock increases.

The first current generation circuit may be further configured to generate the first current in response to a first current section having a nanoampere or a microampere unit of measure among currents injectable into the cranial nerve cell. The second current generation circuit may be further configured to generate the second current in response to a second current section having a picoampere (pA) unit of measure among the currents. The current stimulator may generate the currents by overlapping the first current corresponding to the first output impedance and the second current corresponding to the second output impedance through a parallel connection between the first current generation circuit and the second current generation circuit.

The plurality of transistor pairs may include a first transistor pair configured to output a positive current, and a second transistor pair configured to output a negative current.

The predetermined ratio may include a 10 times ratio.

The second current generation circuit may include a negative feedback path, and may be configured to operate in any one of a first operating mode in which the first current is generated and a second operating mode in which the second current is generated, by controlling the negative feedback path and the first switch and the second switch at the terminals of the capacitor.

The second current generation circuit may be further configured to turn off the negative feedback path; and apply, in response to the first operating mode, the clock to the first switch and the second switch to switch the first switch and the second switch at the terminals of the capacitor to an on state to generate a negative first current, or the clock to the first switch and the second switch to switch the first switch and the second switch at the terminals of the capacitor complementarily on or off to generate a positive first current.

The second current generation circuit may be further configured to turn on the negative feedback path and apply, in response to the second operating mode, the clock to the first switch and the second switch switching the first switch and the second switch at the terminals of the capacitor complementarily on or off to generate the second current.

The capacitor may include a variable capacitor bank with a ¼ times to 4 times variable capacitance.

In another general aspect, an operating method of a current stimulator includes generating a first current injectable into a cranial nerve cell through a current mirroring based on a plurality of transistor pairs comprised in a first current generation circuit; generating a second current smaller than the first current by controlling a charge rate based on a voltage difference between terminals of a capacitor comprised in a second current generation circuit driven by a clock; controlling a first output impedance of the first current generation circuit and a second output impedance of the second current generation circuit to have a magnitude greater than or equal to a predetermined ratio to a load impedance corresponding to the cranial nerve cell; generating currents by overlapping the first current corresponding to the first output impedance and the second current corresponding to the second output impedance; and injecting the generated currents into the cranial nerve cell.

The generating of the second current may include adjusting a magnitude of the second current by controlling the charge rate based on the voltage difference between the terminals of the capacitor disposed between a first switch and a second switch configured to operate complementarily based on a switching of the clock.

The magnitude of the second current may be determined based on any one or any combination of any two or more of a frequency of the clock, a capacitance of the capacitor, and a difference between an input voltage and an output voltage of the second current generation circuit.

The generating of the second current may include generating the second current in response to a second current section in which the magnitude of the second current increases linearly as the frequency of the clock increases.

The predetermined ratio may be a 10 times ratio.

The operating method may further include operating in any one of a first operating mode in which the first current is generated and a second operating mode in which the second current is generated, by controlling a negative feedback path and the first switch and the second switch at the terminals of the capacitor comprised in the second current generation circuit.

The operating in any one of the operating modes may include turning off the negative feedback path and applying the clock to the first switch and the second switch to switch the first switch and the second switch at the terminals of the capacitor to an on state to generate a negative first current to be generated; or turning off the negative feedback path and applying, in response to the first operating mode, the clock to the first switch and the second switch to switch the first switch and the second switch at the terminals of the capacitor complementarily on or off to generate a positive first current to be generated.

The operating in any one of the operating modes may include turning on the negative feedback path and applying, in response to the second operating mode, the clock to the first switch and the second switch to switch the first switch and the second switch at the terminals of the capacitor complementarily on or off to generate the second current.

A non-transitory computer-readable storage medium may store instructions that, when executed by a processor, cause the processor to perform any one of methods herein.

Other features and aspects will be apparent from the following detailed description, the drawings, and the claims.

Figure 1:
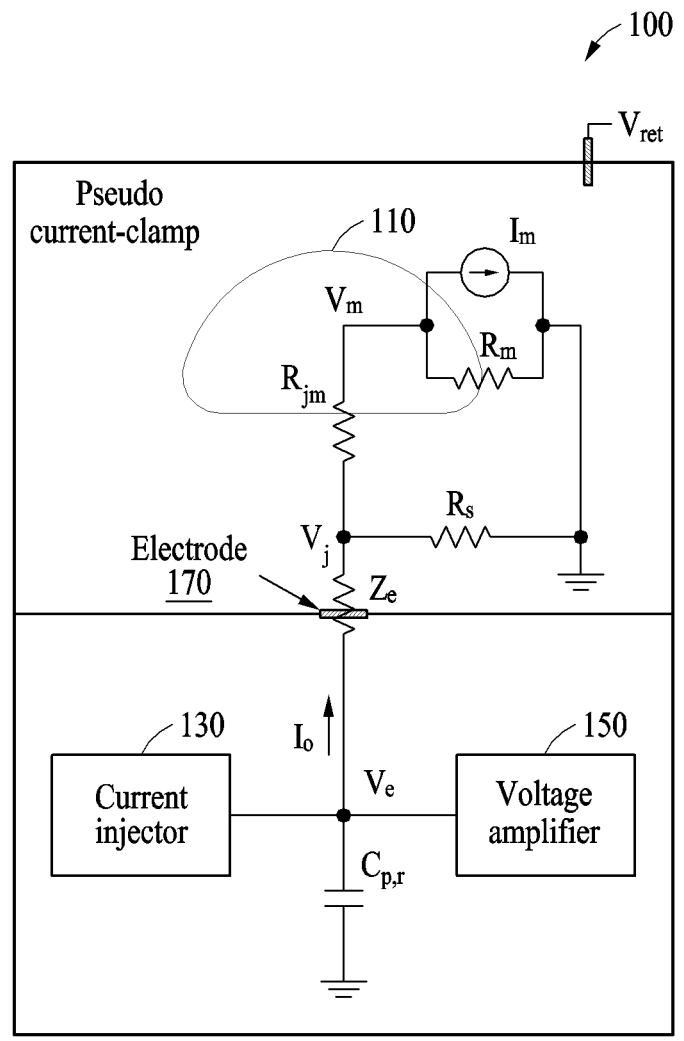
FIG. 1 illustrates an example of a current stimulator providing a current of a predetermined magnitude to a cranial nerve cell.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known after understanding of the disclosure of this application may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween.

As used herein, the term "and/or" includes any one and any combination of any two or more of the associated listed items.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

Spatially relative terms such as "above," "upper," "below," and "lower" may be used herein for ease of description to describe one element's relationship to another element as shown in the figures. Such spatially relative terms are intended to encompass different orientations of the device in use or operation in addition to the orientation depicted in the figures. For example, if the device in the figures is turned over, an element described as being "above" or "upper" relative to another element will then be "below" or "lower" relative to the other element. Thus, the term "above" encompasses both the above and below orientations depending on the spatial orientation of the device. The device may also be oriented in other ways (for example, rotated 90 degrees or at other orientations), and the spatially relative terms used herein are to be interpreted accordingly.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Due to manufacturing techniques and/or tolerances, variations of the shapes shown in the drawings may occur. Thus, the examples described herein are not limited to the specific shapes shown in the drawings, but include changes in shape that occur during manufacturing.

The features of the examples described herein may be combined in various ways as will be apparent after an understanding of the disclosure of this application. Further, although the examples described herein have a variety of configurations, other configurations are possible as will be apparent after an understanding of the disclosure of this application.

FIG. 1 illustrates an example of a current stimulator providing a current to a cranial nerve cell. FIG. 1 illustrates an example 100 showing a current stimulator 130 and a voltage amplifier 150 being connected in parallel to a cranial nerve cell 110 through an electrode 170.

The current stimulator 130 may generate a current Ie and inject the current Ie to the cranial nerve cell 110 through the electrode 170. The cranial nerve cell 110 may perform intracellular binding by the current Ie provided to the cranial nerve cell 110 and induce and/or maintain membrane permeability. The current Ie provided by the current stimulator 130 may compensate for a leakage current inside the cranial nerve cell 110 that is inevitably generated due to the membrane permeabilization of the cranial nerve cell 110. The voltage amplifier 150 may simultaneously measure an electrode voltage Ve, which is an attenuated version of a membrane potential Vm.

An intracellular signal of the cranial nerve cell 110 may be observed, and a signal transmission scheme of the cranial nerve cell 110 may be analyzed based on the current Ie provided by the current stimulator 130. The current stimulator 130 may generate, for example, ultra-fine currents of tens of picoampere (pA) units to currents of tens of nanoampere (nA) units and/or microampere (μA) units with high accuracy to observe intercellular signals of the cranial nerve cell 110, while also reducing noise.

Hereinafter, a structure and an operation of the current stimulator 130 will be described with reference to FIGS. 2 through 11.

Figure 2:
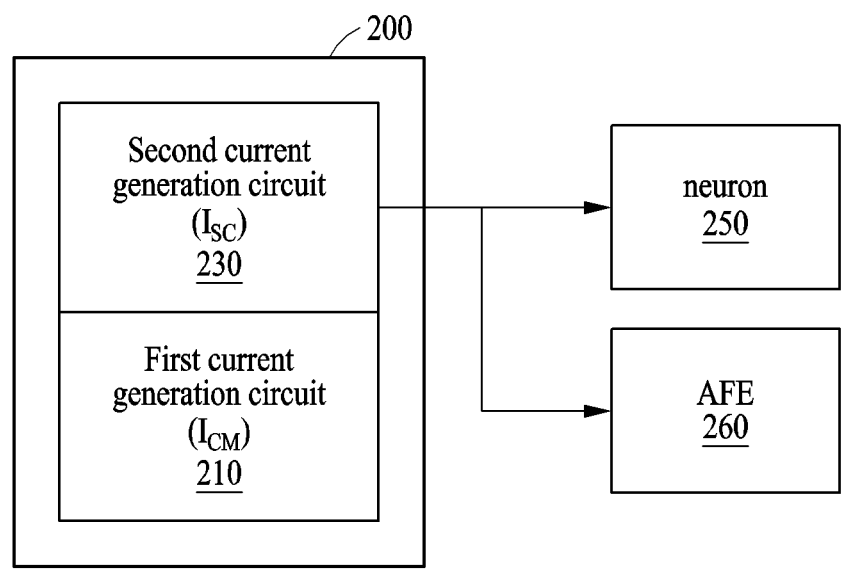
FIG. 2 illustrates an example of a current stimulator.

FIG. 2 illustrates an example of a current stimulator. Referring to FIG. 2, a current stimulator 200 may include a first current generation circuit 210 and a second current generation circuit 230. A current generated by the current stimulator 200 may be provided to a cranial nerve cell, a neuron 250.

The first current generation circuit 210 may generate a first current injected into a cranial nerve cell, the neuron 250, through a current mirroring based on a plurality of transistor pairs. The first current may be expressed as "ICM" since the first current is generated through a current mirroring (CM). Here, the current mirroring may relate to a circuit structure in which a current of the same size is continuously generated by using a transistor as a current source. A current mirroring structure may generate multiple constant current sources by copying a current flowing in an arbitrary circuit and supplying it equally to other circuits. A circuit having a current mirroring structure may be referred to as a current repeater or a current mirror circuit.

For example, the first current generation circuit 210 may generate a first current that shows linearity in all sections regardless of a clock frequency, as illustrated in a graph 330 of FIG. 3 below. The first current generation circuit 210 may generate a first current of a nanoampere (nA) unit and/or a microampere (pA) unit that is injected into the neuron 250 through a current mirroring structure.

The second current generation circuit 230 may be driven by a clock and may generate a second current that is smaller than the first current ICM by controlling a rate of movement of a charge that is caused by a voltage difference between both ends of a capacitor. The second current may be expressed as "ISC" since the second current is generated through a switched capacitor (SC) structure.

For example, the second current generation circuit 230 may generate a second current that is injected into the neuron 250 by a switched capacitor structure. In this example, the switched capacitor structure may be based on a fact that a capacitor that switches at a sufficiently high speed is equivalent to a resistor. In general, a capacitor may store energy as a potential difference between both ends of the capacitor to prevent direct current from flowing. However, when a clock is switched quickly, the capacitor is discharged as soon as it is charged, so the capacitor may operate like a resistor to some extent. Two switches included in the switched capacitor structure may operate by a clock in a complementary but not overlapping manner, that is, when one of the switches is turned on, the other switch is turned off. Assuming that a frequency of a clock applied to the switches is much greater than a period of an input signal, a variation occurring in the input signal may become small enough to ignore.

For example, the second current generation circuit 230 may generate a minute current in a picoampere pA unit as the second current in response to a section in which linearity is shown in line 313 of a graph 310 of FIG. 3 below, which illustrates current I versus frequency f characteristics of the switched capacitor structure.

Here, a first output impedance of the first current generation circuit 210 and a second output impedance of the second current generation circuit 230 may have a magnitude greater than or equal to a predetermined ratio to a load impedance corresponding to the neuron 250 that is a cranial nerve cell. The predetermined ratio may be, for example, a 10 times ratio, however, the examples are not limited thereto.

An analog front end (AFE) 260 may decode a signal generated from the neuron 250 as a current generated by the current stimulator 200 stimulates the neuron 250 into a digital signal. The AFE 260 may correspond to, for example, an analog signal conditioning circuit that uses a sensitive analog amplifier. The AFE 260 may convert a signal generated from the neuron 250 into a digital signal and, for example, transmit the cranial nerve signal to a recording device.

A method of generating a current through the first current generation circuit 210 and the second current generation circuit 230 of the current stimulator 200 is described in detail with reference to FIG. 3 below.

Figure 3:
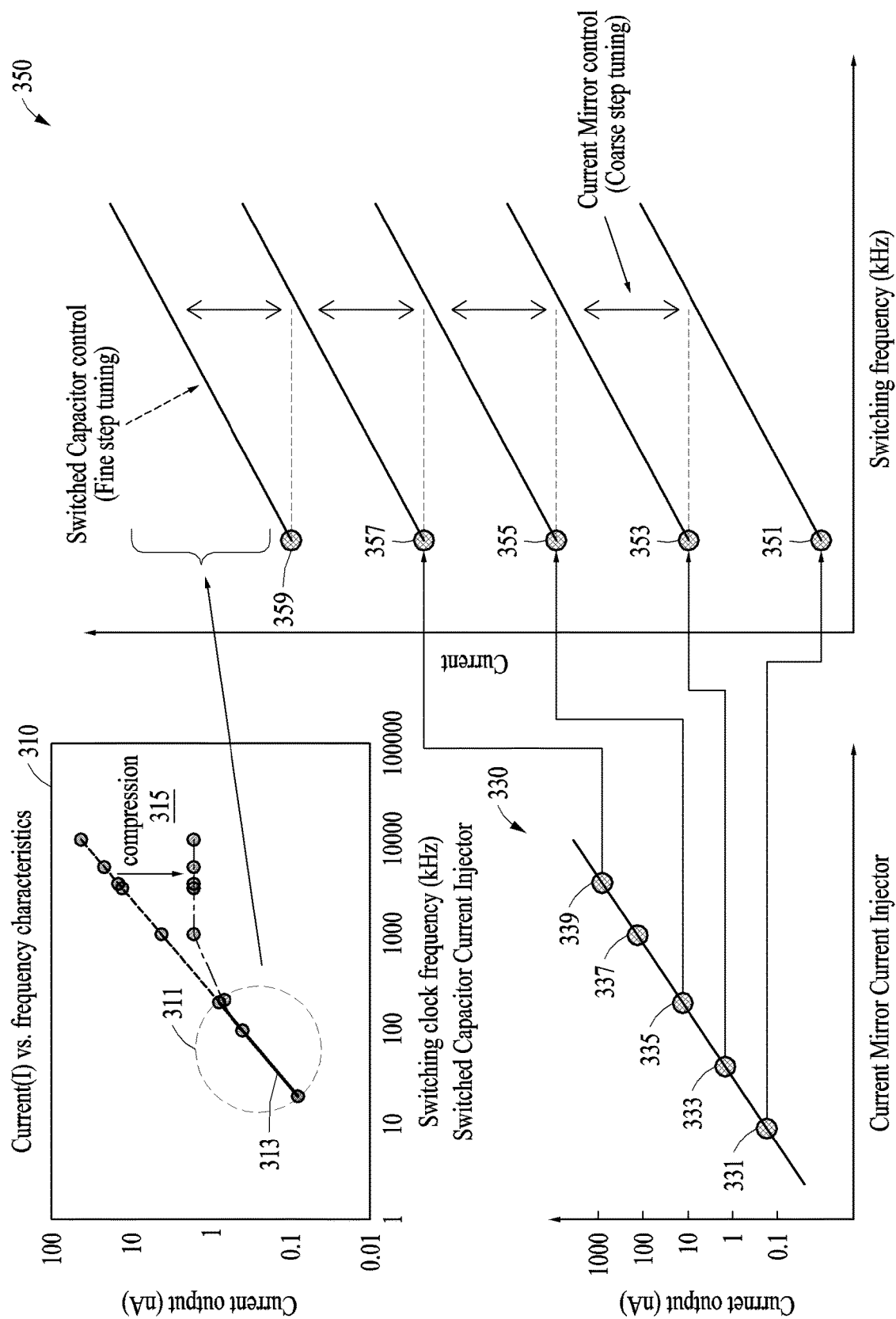
FIG. 3 illustrates an example of a method of generating a current of a current stimulator.

FIG. 3 illustrates an example of a method of generating a current of a current stimulator. FIG. 3 illustrates a graph 310 showing a relationship between a clock frequency f applied to the second current generation circuit and a second current I generated by the second current generation circuit, a graph 330 showing a first current output over time from the first current generation circuit, and a graph 350 showing a relationship between a current overlapping a first current and a second current and a switching frequency of a clock.

If the second current generation circuit has the above-described switched capacitor structure, a relationship between a second current I generated by the second current generation circuit and a clock frequency for switching the second current generation circuit may be expressed as shown in the graph 310.

The generated second current, which is generated in a left section 311 as shown in the graph 310 in which the clock frequency is low, may show linearity as shown in line 313. As shown in the graph 310, the clock frequency may increase toward a right side, and as the clock frequency increases toward a right section 315, the second current may be compressed and show nonlinearity. A current compression that occurs as the clock frequency increases in the second current generation circuit is described in detail with reference to FIG. 7 below.

Therefore, the second current generation circuit may generate a minute second current in a picoampere (pA) unit in which a noise effect of charging and discharging is small, in response to a second current section corresponding to the left section 311 in which the clock frequency is low. The second current generation circuit may generate a second current in response to a magnitude of the second current increasing linearly as a frequency of a clock increases in the second current section.

If the first current generation circuit has the above-described current mirroring structure, the first current generation circuit may generate a first current of a much greater unit (e.g., a nanoampere (nA) or microampere (pA) unit) than the second current generation circuit, as shown in the graph 330. For example, the first current generation circuit may generate a first current corresponding to "0.2" nA 331, "1" nA 333, "10" nA 335, "100" nA 337, and "1000" nA (="1" µA) 339 as shown in the graph 330.

The first current generation circuit may generate the first current in response to a first current section corresponding to an interval of a nanoampere (nA) unit or a microampere (µA) unit among currents that are injected into a cranial nerve cell.

For example, the current stimulator may generate a current injected into a cranial nerve cell through a two-step current generating process as described below.

Through the first current generation circuit, the current stimulator may generate a first current corresponding to points 351, 353, 355, 357, and 359 that have large current units at coarse intervals in the graph 350. For example, the points 351, 353, 355, 357, and 359 may have current values corresponding to "0.2" nA 331, "1" nA 333, "10" nA 335, "100" nA 337, and "1000" nA (="1" µA) 339 in the graph 330, respectively.

Through the second current generation circuit, the current stimulator may generate a minute second current starting at the points 351, 353, 355, 357, and 359 in the graph 350 and having, for example, the same gradient as the line 313 in the graph 310 and a fine interval of a picoampere unit in a frequency section (e.g., 20 kHz to 130 kHz) corresponding to a length of the line 313.

Here, the interval of each of the points 351, 353, 355, 357, and 359 marked on the graph 350 may be controlled by the current mirroring structure of the first current generation circuit. A process of tuning a generation interval of the first current corresponding to the points 351, 353, 355, 357, and 359 may be referred to as coarse step tuning.

In addition, the minute second current generated in the frequency section starting at each of the points 351, 353, 355, 357, and 359 in the graph 350 may be controlled by the switched capacitor structure of the second current generation circuit. A process of tuning a generation interval of the minute second current in the frequency section starting at each of the points 351, 353, 355, 357, and 359 may be referred to as fine step tuning.

The current stimulator may minimize noise by combining the first current generated by the current mirroring structure and the second current generated by the switched capacitor structure into one signal while generating uniform currents ranging from tens of picoamperes (pA) to microamperes (µA) in units of picoamperes. The current stimulator may overlap the first current corresponding to a first output impedance of the first current generation circuit and the second current corresponding to a second output impedance of the second current generation circuit through a parallel connection between the first current generation circuit and the second current generation circuit. For example, a current generated by the current stimulator may be expressed as $I = I_{fine\text{-}step\ current\ from\ SC} + I_{coarse\text{-}step\ current\ from\ CM}$.

An example of a circuit configuration of a current stimulator is described in detail with reference to FIG. 4 below.

Figure 4:
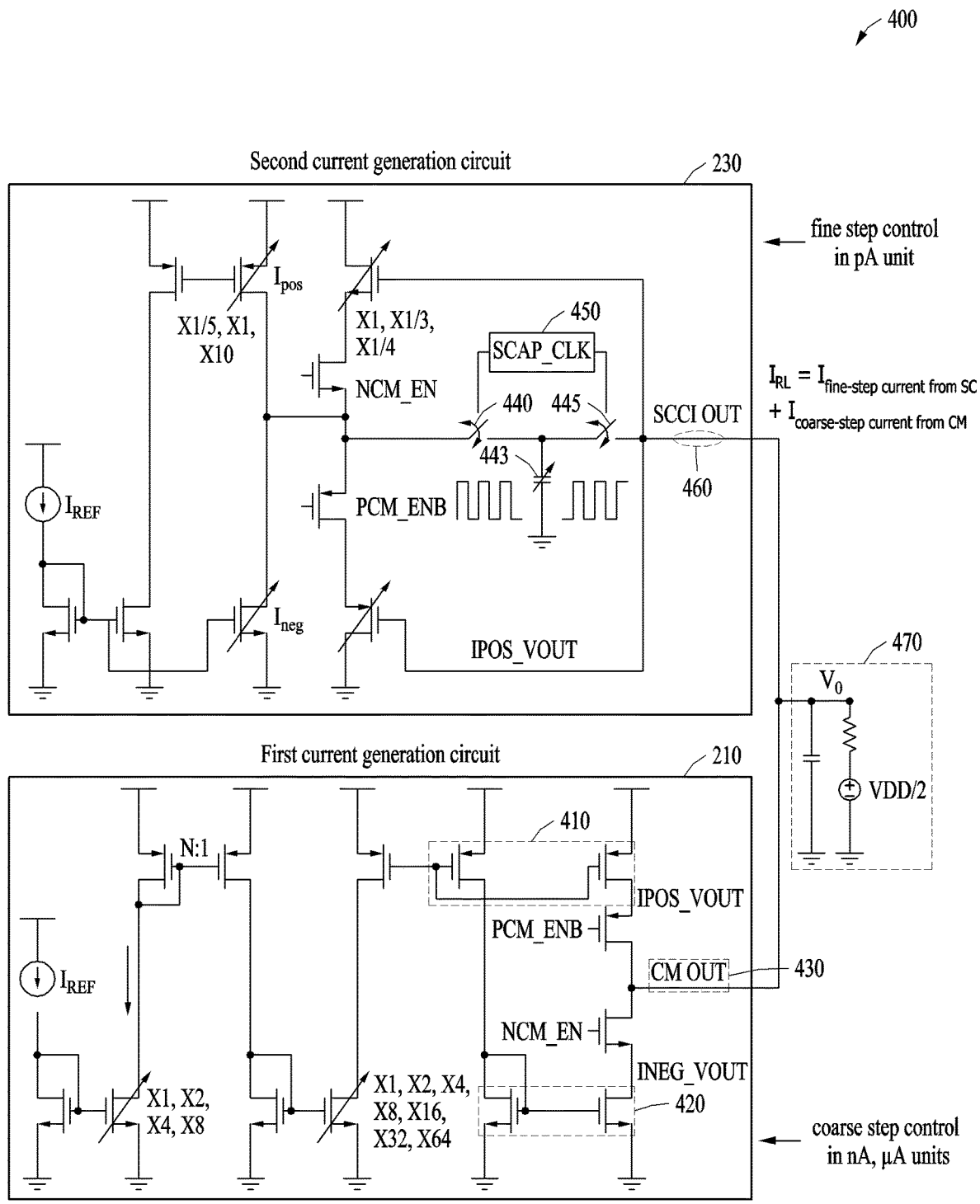
FIG. 4 illustrates an example of a circuit configuration of a current stimulator.

FIG. 4 illustrates an example of a circuit configuration of a current stimulator. FIG. 4 illustrates an example of a current IRL generated through a current stimulator 400, including a first current generation circuit 210 and a second current generation circuit 230 is provided to a load 470 corresponding to a cranial nerve cell 110.

The first current generation circuit 210 may include, for example, a first transistor pair 410 in a current mirroring structure in which a positive current IPOS is output from a positive voltage IPOS_VOUT and a second transistor pair 420 in a current mirroring structure in which a negative current INEG is output from a negative voltage INEG_VOUT. Here, a current copied through the first transistor pair 410 may be output to an output terminal CM OUT 430 as a transistor PCM_ENB is enabled. The first current generation circuit 210 may generate a first current injected into the load 470 corresponding to a cranial nerve cell through a current mirroring based on a plurality of transistor pairs 410 and 420.

The second current generation circuit 230 may include a first switch 440 and a second switch 445, and a capacitor 443. The first switch 440 and the second switch 445 may operate in a complementary manner in conjunction with a switching of a clock SCAP_CLK 450. For example, if the first switch 440 is on, the second switch 445 may be off. In another example, if the first switch 440 is off, the second switch 445 may be on. The capacitor 443 may be disposed between the first switch 440 and the second switch 445 to charge and/or discharge a charge according to the switching of the clock 450.

The second current generation circuit 230 may evenly adjust a magnitude of a second current by controlling a rate of movement of a charge that is caused by a voltage difference between both ends of the capacitor 443.

The magnitude of the second current may be determined based on, for example, any one or any combination of a frequency f of the clock 450, a capacitance c of the capacitor 443, and a voltage difference V between an input voltage and an output voltage of an output terminal SCCI OUT 460 of the second current generation circuit 230.

Here, a first output impedance corresponding to the output terminal CM OUT 430 of the first current generation circuit 210 and a second output impedance corresponding to the output terminal 460 of the second current generation circuit 230 may have a magnitude greater than or equal to a predetermined ratio to an impedance of the load 470 corresponding to a cranial nerve cell. The predetermined ratio may include, for example, a 10 times ratio; however, the examples are not limited thereto.

In an example, a magnitude of an output impedance of each current generation circuit compared to the impedance of the load 470 may be very large so that a current generated by each of the current generation circuits may not be affected.

The current stimulator 400 may generate a current IRL by overlapping a first current ICM corresponding to the first output impedance and a second current ISC corresponding to the second output impedance through a parallel connection between the first current generation circuit 210 and the second current generation circuit 230.

Figure 5:
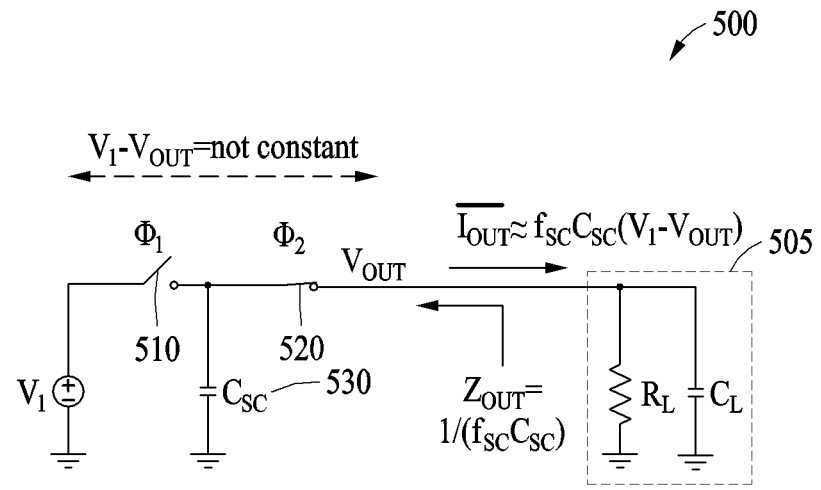
FIG. 5 illustrates an example of an operation principle of a second current generation circuit.

FIG. 5 illustrates an example of an operation principle of a second current generation circuit. Referring to FIG. 5, a second current generation circuit 500 may include a first switch 510, a second switch 520, and a capacitor 530.

The first switch 510 may be driven by a switching clock $\phi_1$. In addition, the second switch 520 may be driven by a switching clock $\phi_2$. Here, the switching clock $\phi_1$ and the switching clock $\phi_2$ may complement each other.

The capacitor 530 may charge and/or discharge a charge of a capacitance C. For example, the capacitor 530 may be charged with a quantity of electric charge Q equal to a capacitance C of the capacitor x a voltage V. If a voltage difference between both ends of the capacitor 530 is (V1−Vout), the quantity of electric charge Q may be calculated as Q=C×(V1−Vout).

Here, current I corresponds to a quantity of electric charge transferred per unit of time, so a second current generated by the second current generation circuit 500 may be expressed in Equation 1 below.

$$I = dQ/dt = C \times V/(1/f) = C \times V \times f \quad \text{[Equation 1]}$$

It can be seen from Equation 1 that the magnitude of the second current generated by the second current generation circuit 500 may be determined based on any one or any combination of a frequency f of a clock, a capacitance C of the capacitor 530, and a difference V between an input voltage and an output voltage of the second current generation circuit.

For example, if a voltage difference equal to (V1−Vout) occurs between the two ends of the capacitor 530, a charge corresponding to a quantity of electric charge $Q_{SC}$ may be moved in the second current generation circuit 500. Here, the second current generation circuit 500 may control a rate at which the charge is transferred through, for example, software.

A current $I_{OUT} \approx f_{SC} C_{SC}(V_1 - V_{OUT})$ generated through the second current generation circuit 500 may be provided to a load 505 corresponding to a cranial nerve cell. Here, the load 505 may be a model of electrical characteristics of the cranial nerve cell using a resistor R and a capacitor C. A second output impedance $Z_{OUT}$ of the second current generation circuit 500 viewed from the load 505 side may be expressed as $Z_{OUT} = 1/(f_{SC} C_{SC})$.

The second current generation circuit 500 may control the second output impedance $Z_{OUT}$ to have a magnitude greater than or equal to a predetermined ratio (e.g., 10 times) to an impedance of the load 505. Characteristics of an operation of the second current generation circuit 500 are described in detail with reference to FIG. 6 below.

Figure 6:
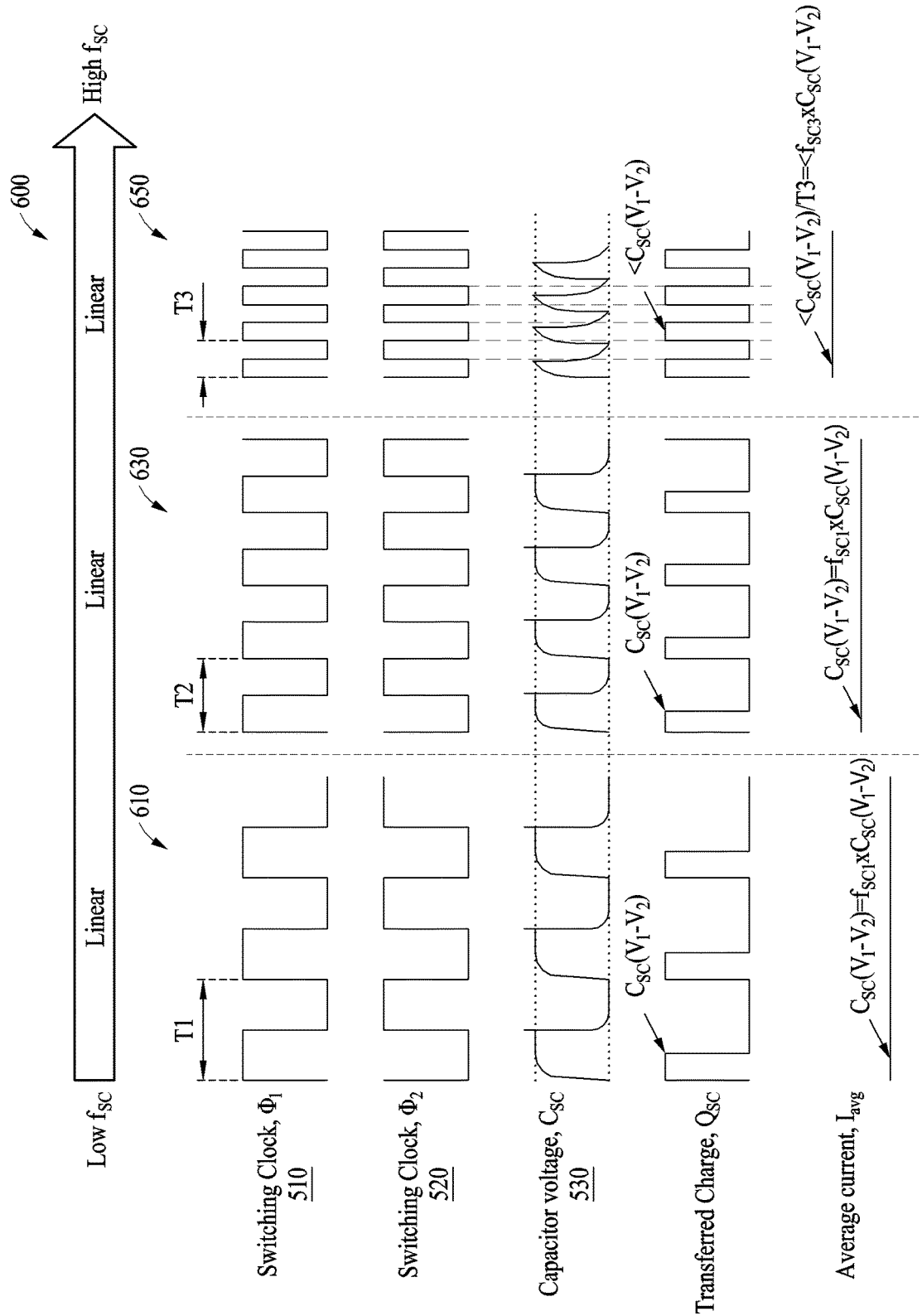
FIG. 6 illustrates an example of a relationship between a current generated from a second current generation circuit and a frequency of a clock.

FIG. 6 illustrates an example of a relationship between a current generated from a second current generation circuit and a frequency of a clock. Graphs 610, 630, and 650 in FIG. 6 show a relationship between a switching clock $\phi_1$ applied to a first switch 510, a switching clock $\phi_2$ applied to a second switch 520, a voltage Vsc of a capacitor 530, a quantity of electric charge $Q_{SC}$ of the capacitor 530, and an average current $I_{avg}$ of the second current generation circuit in response to a switching frequency $f_{sc}$ of the clock being gradually changed from a low frequency to a high frequency.

As described above, the first switch 510 and the second switch 520 may operate in a complementary manner with respect to each other, and for this purpose, the switching clock $\phi_1$ and the switching clock $\phi_2$ applied to the first switch 510 and the second switch 520 may operate in a complementary manner with respect to each other.

In an example, the switching clocks $\phi_1$ and $\phi_2$ may have a T1 period, as shown in the graph 610. When the first switch 510 is closed by the switching clock $\phi_1$, the second switch 520 may be opened by the switching clock $\phi_2$. In this example, a voltage Vsc may be provided to the capacitor 530 until the first switch 510 is opened, and accordingly, a quantity of electric charge $Q_{SC}$ ($V_1 - V_2$) corresponding to a voltage difference between both ends of the capacitor 530 may be charged. Here, the average current $I_{avg}$ generated by charges moved by the clocks switched in the T1 period may be expressed as, for example, $C_{SC}(V_1 - V_2)/T1 = f_{SC1} \times C_{SC}(V_1 - V_2)$.

The switching frequency $f_{sc}$ of a clock may be changed to a T2 period as shown in the graph 630, or a T3 period as shown in the graph 650. Here, a switching period of the clock may have, for example, a size such as T1>T2>T3.

For example, when a period of the switching frequency of a clock is the T2 period, the average current $I_{avg}$ generated by a charge moved by a clock switched in the T2 period as shown in the graph 630 may be expressed as $C_{SC}(V_1 - V_2)/T2 = f_{SC2} \times C_{SC}(V_1 - V_2)$.

As the switching frequency of a clock increases, that is, as the switching period of the clock decreases, a transfer rate of a charge may also increase in proportion to the switching speed of the clock. Accordingly, since more current may move within a unit of time, a magnitude of a current may also increase.

In addition, as shown in the graph 650, when a period of the switching frequency of a clock is the T3 period, the average current $I_{avg}$ generated by a charge moved by a clock switched in the T3 period may be expressed as $C_{SC}(V_1 - V_2)/T3 = f_{SC3} \times C_{SC}(V_1 - V_2)$. As shown in the graph 650, when the switching period of a clock is the T3 period, a charging time may be very short and the charge in the capacitor 530 may be discharged before being sufficiently charged.

As described above, when the charging and/or discharging time of a charge becomes insufficient as the switching frequency increases, the charge may not be sufficiently provided to the capacitor 530, and accordingly, a magnitude of the average current $I_{avg}$ may be compressed with respect to the frequency and may have a nonlinear characteristic. Nonlinear characteristics that appear according to a magnitude of the switching frequency are described in detail with reference to FIG. 7 below.

In addition, due to an operation principle of the second current generation circuit, the transfer of a charge may not occur linearly and evenly, but may follow an exponential curve according to a resistor-capacitor (RC) time constant of a source or a load. As a result, a ripple may occur in an output current or an output voltage of the second current generation circuit. For example, a ripple in a sawtooth shape may repeatedly occur at every clock cycle up to a magnitude of around 6 mV, and accordingly, a ripple may act as noise in response to a signal sampling of the analog front end (AFE) 260 mentioned above with reference to FIG. 2.

In an example, since an external clock frequency may control a second current generated by the second current generation circuit, a second current generated by the second current generation circuit may be used in a frequency section that has a linear characteristic, and a first current generated by a first current generation circuit may be used in a frequency section in which the second current generation circuit has a nonlinear characteristic to reduce noise while generating uniform currents.

Figure 7:
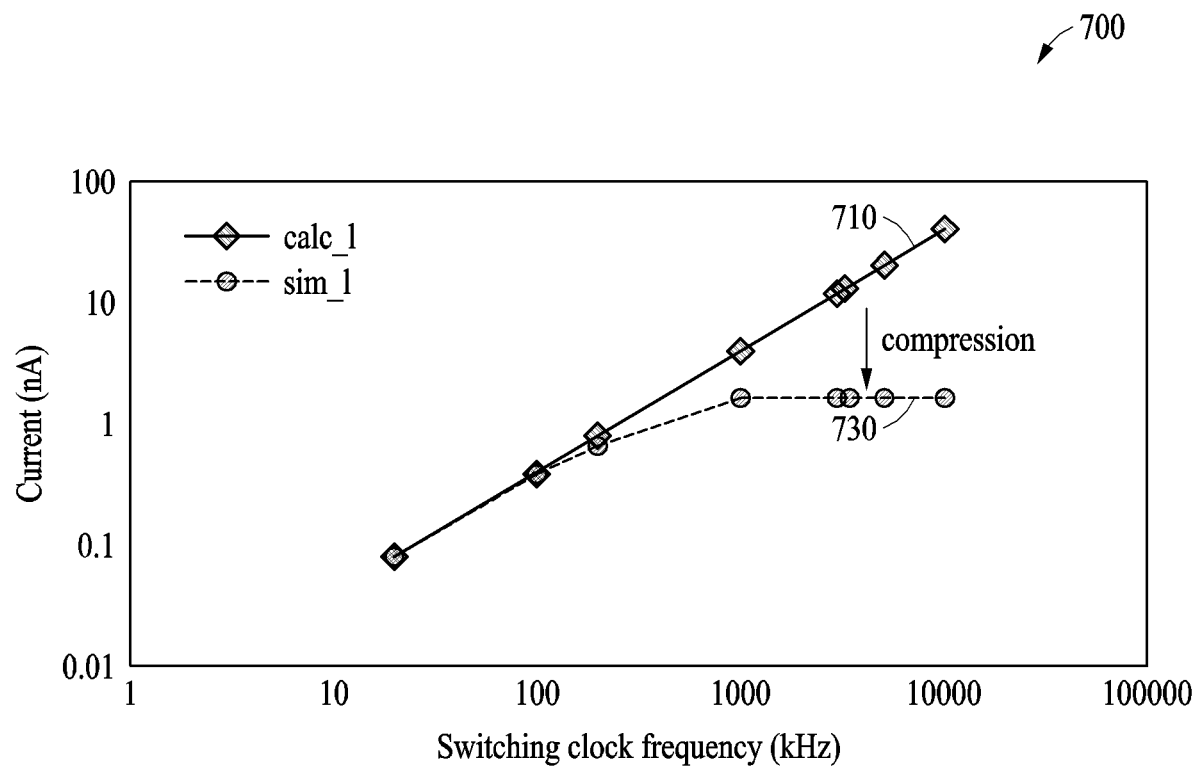
FIG. 7 illustrates an example of a current compression occurring in a second current generation circuit.

FIG. 7 illustrates an example of a current compression occurring in a second current generation circuit. In addition, FIG. 7 illustrates an example 700 of a difference between a graph 710 showing a magnitude of a current calc_I calculated in response to assuming that an ideal switch is used in the second current generation circuit and a graph 730 showing a magnitude of a current sim_I calculated according to a result of simulating the actual second current generation circuit.

The second current generation circuit with a switched capacitor structure may uniformly generate a minute current for a plurality of electrodes. In an example, a capacitance Csc of a capacitor in the second current generation circuit may be 15.9 f, a voltage Vsc of the capacitor may be 153 mV, and a frequency fsc of a clock may be 20 kHz to 10,240 kHz. In this example, as a magnitude of the current calc_I equals Csc×Vsc×fsc, a magnitude of a current generated by a second current generation circuit that has an ideal switch may equal 15.9 f×153 mV×(20 kHz~10,240 kHz), and may show linearity as shown in the graph 710.

As a switching frequency increases in the second current generation circuit with a switched capacitor structure, an instantaneous curve of charge and/or discharge may act as noise and a driving clock may act as a spur. Accordingly, in an example of the current sim_I generated by the actual second current generation circuit, a characteristic of an increase in current in proportion to a frequency may also have a characteristic of being saturated, as shown in the graph 730 since compression occurs along with an increase in frequency.

In addition, since the second current generation circuit has a structure in which a capacitor switching is performed by a clock, when a current increases due to clock driving, current consumption by the clock may increase simultaneously. For example, when a current is 1 nanoampere (nA) or less, current consumption by the clock becomes 100 nanoampere (nA) or less, but when a current is greater than 1 nanoampere (nA), current consumption by the clock may rapidly increase in microampere units.

Therefore, the second current generation circuit may use a second current generated by the second current generation circuit in a frequency section with a linear characteristic and a current section of a predetermined magnitude or less.

Figure 8:
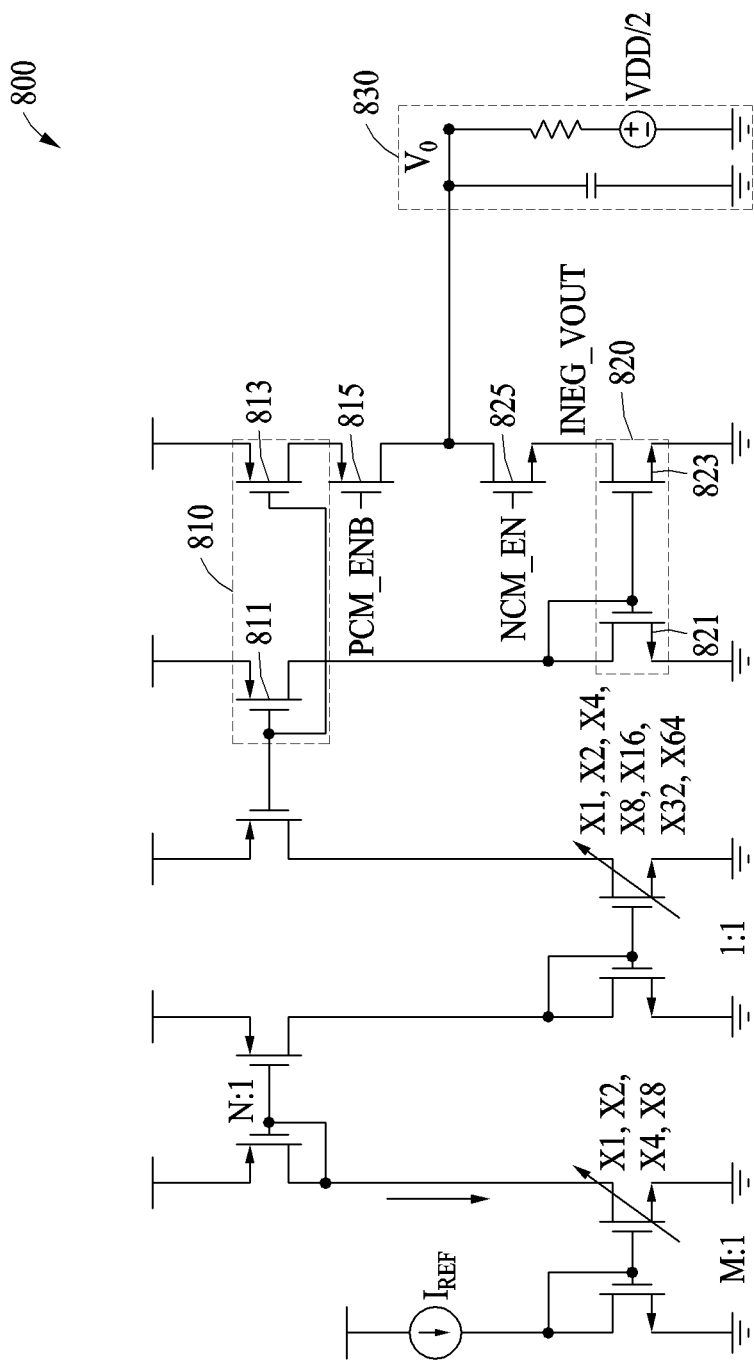
FIG. 8 illustrates an example of an operation of a first current generation circuit.

FIG. 8 illustrates an example of an operation of a first current generation circuit. FIG. 8 illustrates a structure of the first current generation circuit 800, including first transistor pairs 810 configured to output a positive current and second transistor pairs 820 configured to output a negative current through a current mirroring structure. A first current generated by the first current generation circuit 800 may be provided to a load 830 corresponding to a cranial nerve cell.

A 1-1 transistor 811 and a 1-2 transistor 813 constituting the first transistor pairs 810 may correspond to a current mirroring structure that outputs a positive current, and a 2-1 transistor 821 and a 2-2 transistor 823 constituting the second transistor pairs 820 may constitute a current mirroring structure that outputs a negative current.

For example, a voltage of a drain and a gate of the 1-1 transistor 811 among the first transistor pairs 810 may be Vx. The voltage Vx may be applied to the 1-2 transistor 813, and accordingly, a positive current copied, equal to a current applied to the 1-1 transistor 811, may be generated in the 1-2 transistor 813. The positive current generated in the 1-2 transistor 813 may be provided to the load 830 as a 1-3 transistor PCM_ENB 815 is enabled.

Similarly, a voltage of a drain and a gate of the 2-1 transistor 821 among the second transistor pairs 820 may be Vx. The voltage Vx may be applied to the 2-2 transistor 823, and accordingly, a negative current copied, equal to a current applied to the 2-1 transistor 821, may be generated in the 2-2 transistor 823. The negative current generated in the 2-2 transistor 823 may be provided to the load 830 as a 2-3 transistor NCM_EN 825 is enabled. Thus, the first current generation circuit 800 with a current mirroring structure may output a positive current and a negative current.

Since the first current generation circuit 800 copies a current through the current mirroring structure, current consumption is low compared to a switched capacitor structure, and nanoampere or microampere unit currents may be generated without ripples that occur in the switched capacitor structure. In addition, the first current generation circuit 800 may be driven without a clock, so there may be no increase in power consumption generated by the clock due to an increase in current.

In an example, by raising an output impedance of the first current generation circuit 800 to, for example, several giga ohms, current loss may be prevented during a parallel coupling with a second current generation circuit with a switched capacitor structure.

Figure 9A:
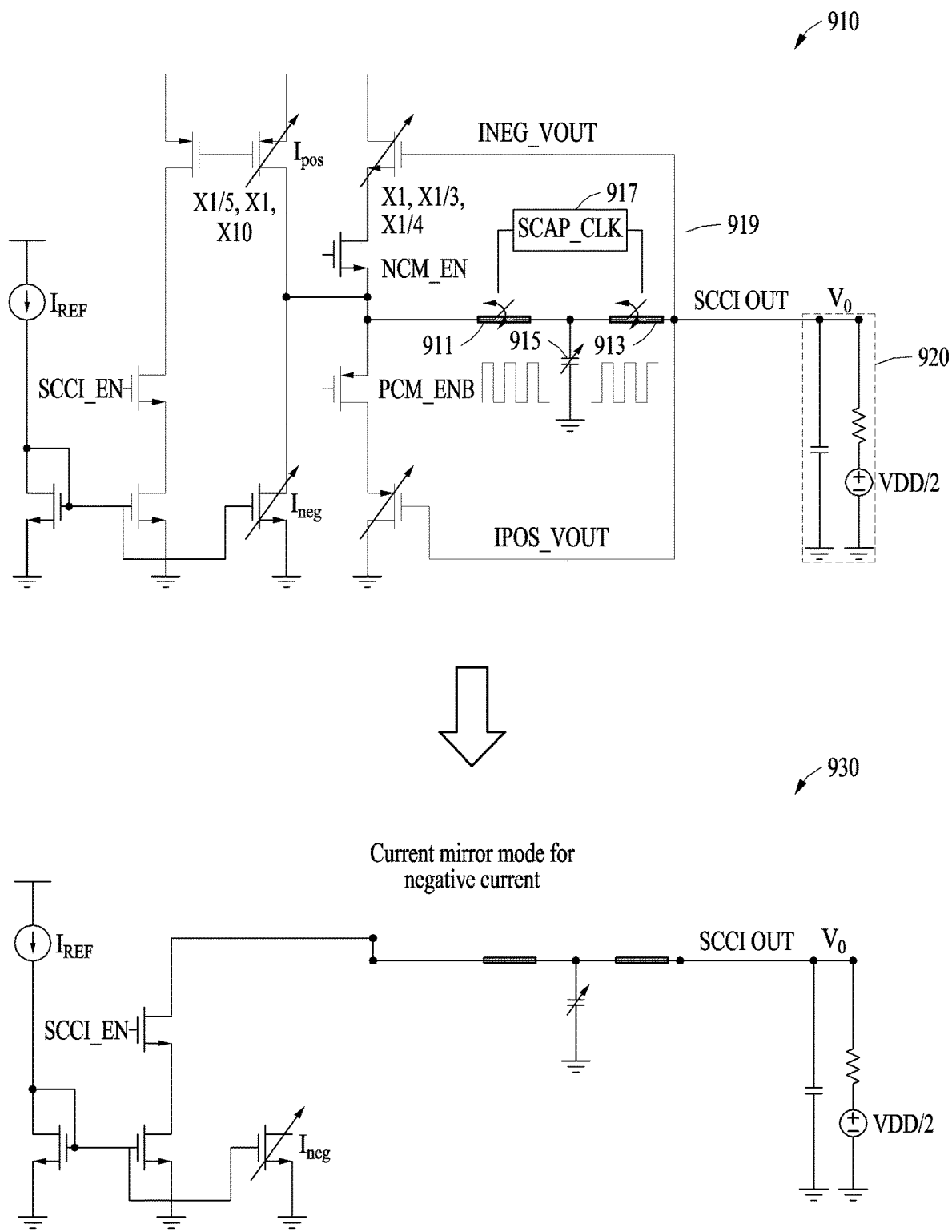
FIGS. 9A and 9B illustrate an example of a second current generation circuit operating in a dual mode in which a first current and a second current are generated.
Figure 9B:
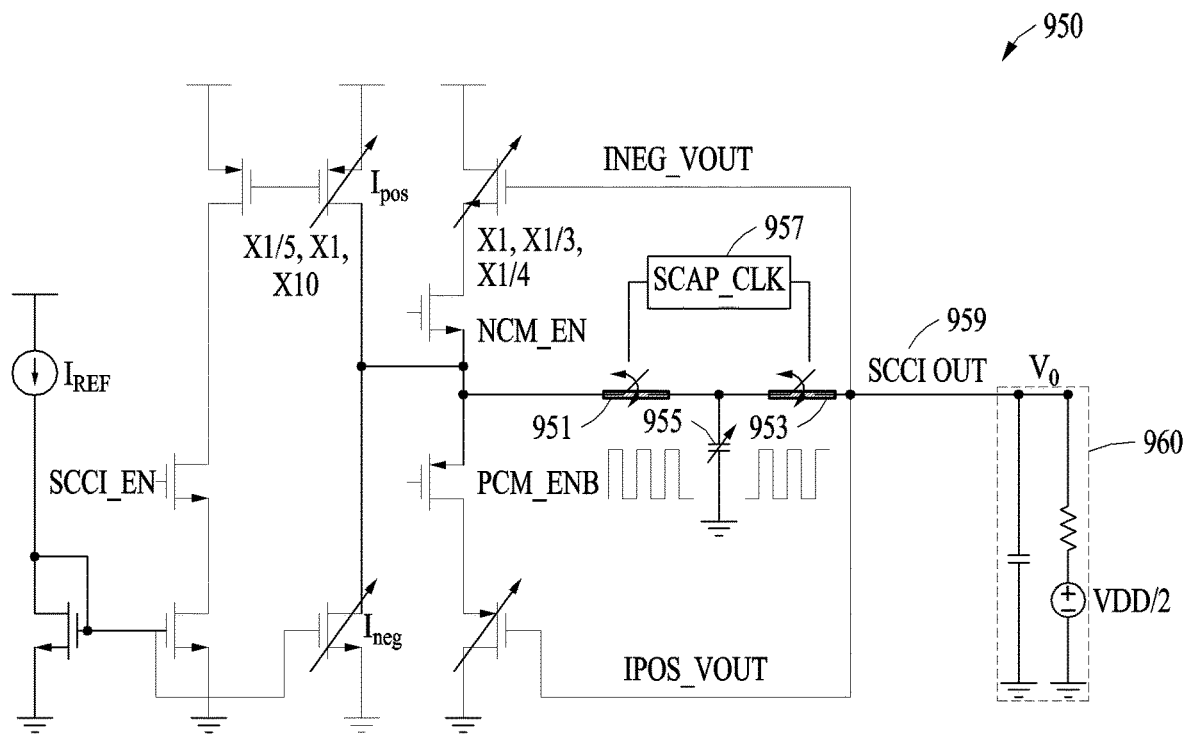
Figure 9B:
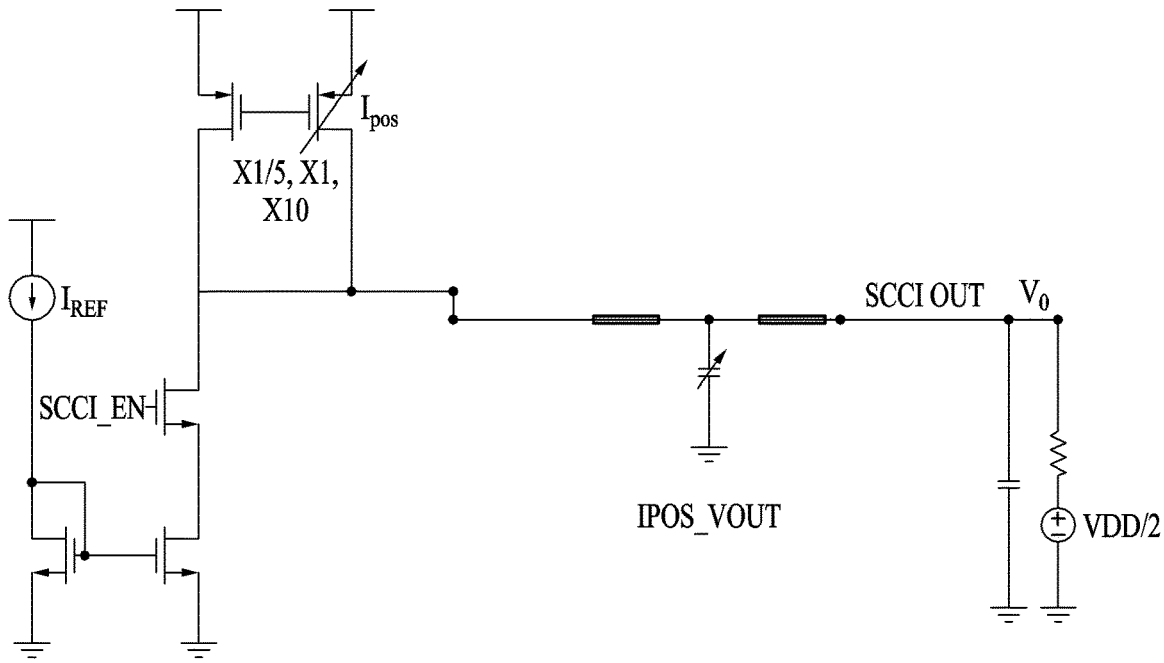

FIGS. 9A and 9B illustrate an example of a second current generation circuit operating in a dual mode in which a first current and a second current are generated.

The second current generation circuit may include a negative feedback path and may be configured to operate in any one of a first operating mode in which the first current is generated and a second operating mode in which the second current is generated, by controlling the negative feedback path and the first switch and the second switch on the two ends of the capacitor. Here, the negative feedback path may correspond to a circuit in which the fed back current affects an input current and proceeds in a direction to reduce the fed back current.

For example, the second current generation circuit may turn on the negative feedback path and, as described above, apply a clock to the first switch and the second switch so that the first switch and the second switch on both ends of a capacitor are on or off in a complementary manner to cause the second current to be generated, in response to the operating mode being set to the second operating mode.

An operation of the second current generation circuit in which the operating mode is set to the first operating mode is described with reference to FIGS. 9A and 9B below.

FIG. 9A illustrates a structure of an equivalent circuit 930 in which the operating mode of a second current generation circuit 910 is set to the first operating mode and set to generate a negative current.

The second current generation circuit 910, for example, may turn off the negative feedback path in response to the operating mode being set to the first operating mode.

The second current generation circuit 910 may apply a same clock value to a first switch 911 and a second switch 913 by a clock 917 so that the first switch 911 and the second switch 913 on both ends of a capacitor 915 are always in an on state to cause a negative first current to be generated. For example, the second current generation circuit 910 may apply a same clock so that a VDD and the switches 911 and 913 on the two ends of the capacitor 915 are always in the on state to cause the negative first current INEG to be provided to a load 920. In an example in which the second current generation circuit 910 is configured to generate the negative first current INEG, the second current generation circuit 910 may operate like the equivalent circuit 930.

FIG. 9B illustrates a structure of an equivalent circuit 970 in which the operating mode of a second current generation circuit 950 is set to the first operating mode and set to generate a positive current.

The second current generation circuit 950, for example, may turn off the negative feedback path in response to the operating mode being set to the first operating mode.

The second current generation circuit 950 may apply a complementary clock value to a first switch 951 and a second switch 953 by a clock 957 so that the first switch 951 and the second switch 953 on both ends of a capacitor 955 are on or off in a complementary manner to cause a positive first current to be generated. For example, the second current generation circuit 950 may apply a clock so that a VSS and the switches on the two ends of the capacitor 955 are on or off in a complementary manner to cause the positive first current IPOS to be provided to a load 960. In an example in which the second current generation circuit 950 is configured to generate the positive first current IPOS, the second current generation circuit 950 may operate like the equivalent circuit 970.

Figure 10:
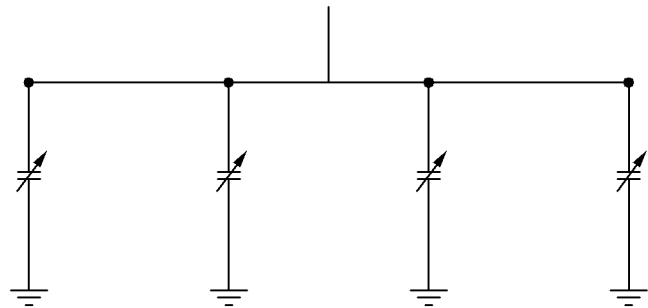
FIG. 10 illustrates an example of a second current generation circuit, including a variable capacitor bank.
Figure 10:
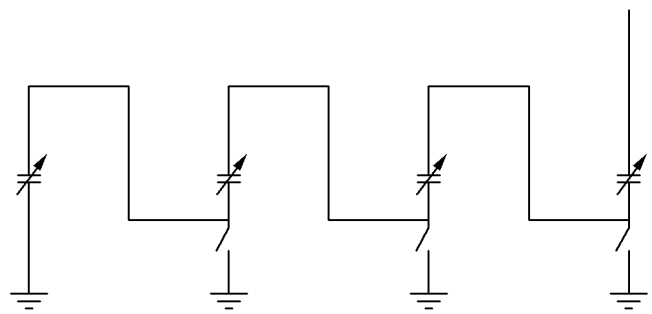

FIG. 10 illustrates an example of a second current generation circuit including a variable capacitor bank.

A capacitor included in the second current generation circuit may include a variable capacitor bank in which a capacitance of the capacitor may change, for example, 4 times, as shown in an example 1010. In another example, a capacitor included in the second current generation circuit may include a variable capacitor bank in which a capacitance of the capacitor may change, for example, ¼ times as shown in an example 1030.

In an example, a capacitor included in the second current generation circuit may be configured as a variable capacitor bank to reduce a size of a switched capacitor and allow the capacitor to have a wide variable capacitance.

Figure 11:
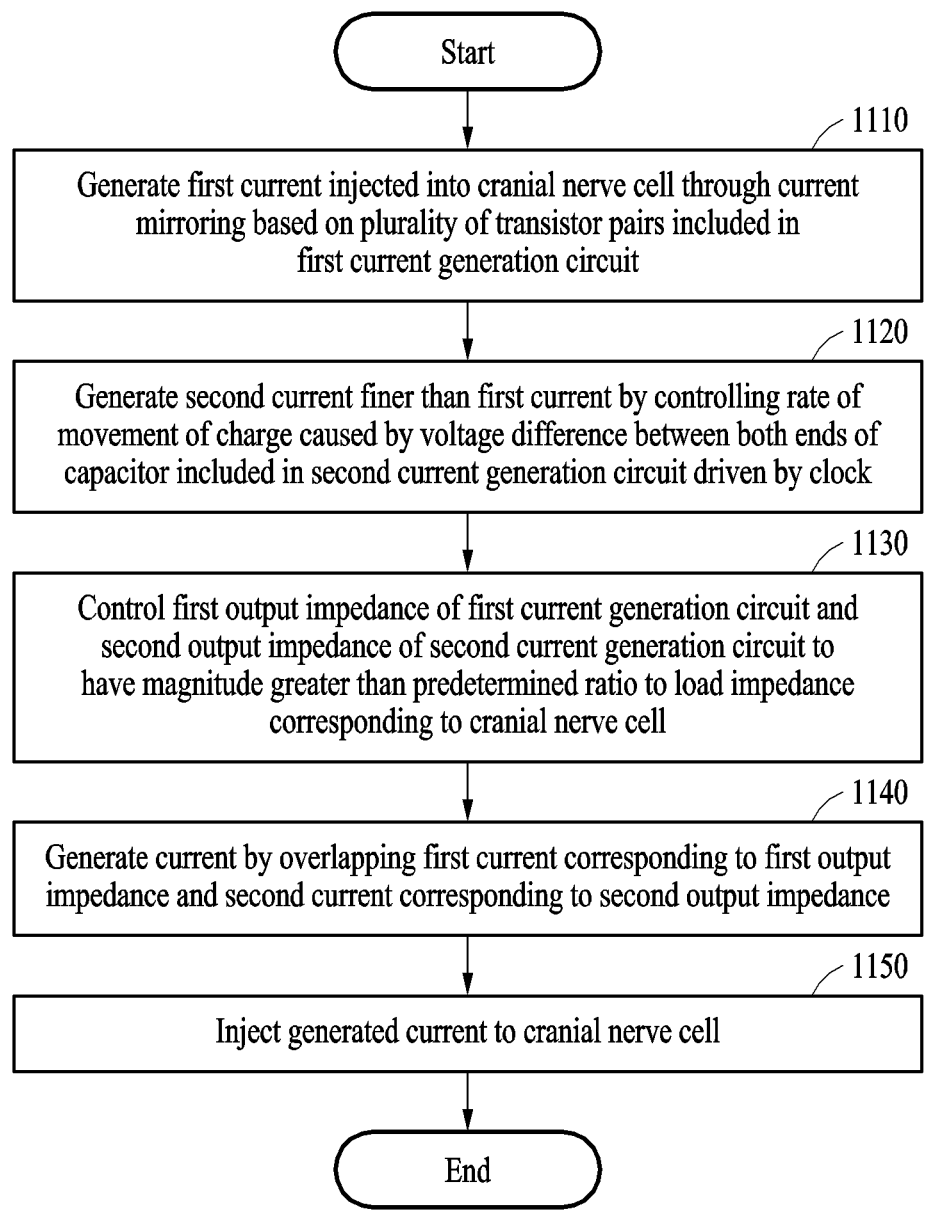
FIG. 11 illustrates an example of an operating method of a current stimulator.

FIG. 11 illustrates an example of an operating method of a current stimulator. Referring to FIG. 11, the current stimulator may generate a current injected into a cranial nerve cell through operations 1110 through 1150.

In operation 1110, the current stimulator may generate a first current injected into a cranial nerve cell through a current mirroring that is based on a plurality of transistor pairs included in a first current generation circuit.

In operation 1120, the current stimulator may generate a second current that is smaller than the first current by controlling a rate of movement of a charge that is caused by a voltage difference between both ends of a capacitor included in a second current generation circuit driven by a clock. For example, the current stimulator may evenly adjust the magnitude of the second current by controlling the rate of movement of a charge that is caused by the voltage difference between the two ends of the capacitor disposed between a first switch and a second switch configured to operate in a complementary manner in conjunction with a switching of the clock. The magnitude of the second current may be determined based on, for example, any one or any combination of a frequency f of the clock, a capacitance c of the capacitor, and a difference V between an input voltage and an output voltage of the second current generation circuit. The current stimulator may generate the second current in response to a second current section in which the magnitude of the second current increases linearly as the frequency of the clock increases.

According to an example, the capacitor may include a variable capacitor bank in which the capacitance of the capacitor may change ¼ times to 4 times.

In operation 1130, the current stimulator may control a first output impedance of the first current generation circuit and a second output impedance of the second current generation circuit to have a magnitude greater than or equal to a predetermined ratio to a load impedance corresponding to a cranial nerve cell. The predetermined ratio may include, for example, a 10 times ratio.

In operation 1140, the current stimulator may generate a current by overlapping the first current corresponding to the first output impedance and the second current corresponding to the second output impedance controlled through operation 1130.

In operation 1150, the current stimulator may inject the current generated in operation 1140 to a cranial nerve cell.

According to an example, the current stimulator may operate in any one of a first operating mode in which the first current is generated and a second operating mode in which the second current is generated, by controlling a negative feedback path and the first switch and the second switch on the two ends of the capacitor included in the second current generation circuit.

For example, the current stimulator may turn off the negative feedback path and apply the clock to the first switch and the second switch so that the first switch and the second switch on the two ends of the capacitor are always in an on state to cause a negative first current to be generated. In another example, the current stimulator may turn off the negative feedback path and apply the clock to the first switch and the second switch so that the first switch and the second switch on the two ends of the capacitor are on or off in a complementary manner to cause a positive first current to be generated, in response to the operating mode being set to the first operating mode.

In response to the operating mode being set to the second operating mode, the current stimulator may turn on the negative feedback path and apply the clock to the first switch and the second switch so that the first switch and the second switch on the two ends of the capacitor are on or off in a complementary manner to cause the second current to be generated.

The current stimulator in FIGS. 1-11 that perform the operations described in this application are implemented by hardware components configured to perform the operations described in this application that are performed by the hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-11 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions in the specification, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:
1. A current stimulator, comprising:
    a first current generation circuit configured to generate a first current of currents, injectable into a cranial nerve cell, through a current mirroring based on a plurality of transistor pairs; and a second current generation circuit, driven by a clock, configured to generate a second current of the currents smaller than the first current by controlling a charge rate based on a voltage difference between terminals of a capacitor, wherein a first output impedance of the first current generation circuit and a second output impedance of the second current generation circuit have a magnitude greater than or equal to a predetermined ratio to a load impedance corresponding to the cranial nerve cell.

2. The current stimulator of claim 1, wherein the second current generation circuit comprises a first switch and a second switch configured to operate complementarily based on a switching of the clock, and wherein the capacitor, disposed between the first switch and the second switch, is configured to adjust a magnitude of the second current by controlling the charge rate.

3. The current stimulator of claim 2, wherein the magnitude of the second current is determined based on any one or any combination of any two or more of a frequency of the clock, a capacitance of the capacitor, and a difference between an input voltage and an output voltage of the second current generation circuit.

4. The current stimulator of claim 1, wherein the second current generation circuit is further configured to generate the second current in a second current section in which the magnitude of the second current increases linearly as a frequency of the clock increases.

5. The current stimulator of claim 1, wherein the first current generation circuit is further configured to generate the first current in response to a first current section having a nanoampere or a microampere unit of measure among the currents injectable into the cranial nerve cell, the second current generation circuit is further configured to generate the second current in response to a second current section having a picoampere (pA) unit of measure among the currents, and the current stimulator generates the currents by overlapping the first current corresponding to the first output impedance and the second current corresponding to the second output impedance through a parallel connection between the first current generation circuit and the second current generation circuit.

6. The current stimulator of claim 1, wherein the plurality of transistor pairs comprises:

a first transistor pair configured to output a positive current; and a second transistor pair configured to output a negative current.

7. The current stimulator of claim 1, wherein the predetermined ratio comprises a 10 times ratio.

8. The current stimulator of claim 1, wherein the second current generation circuit comprises a negative feedback path, and is configured to operate in any one of a first operating mode in which the first current is generated and a second operating mode in which the second current is generated, by controlling the negative feedback path and the first switch and the second switch at the terminals of the capacitor.

9. The current stimulator of claim 8, wherein the second current generation circuit is further configured to:

turn off the negative feedback path; and apply, in response to the first operating mode, the clock to the first switch and the second switch to switch the first switch and the second switch at the terminals of the capacitor to an on state to generate a negative first current, or the clock to the first switch and the second switch to switch the first switch and the second switch at the terminals of the capacitor complementarily on or off to generate a positive first current.

10. The current stimulator of claim 8, wherein the second current generation circuit is further configured to turn on the negative feedback path and apply, in response to the second operating mode, the clock to the first switch and the second switch switching the first switch and the second switch at the terminals of the capacitor complementarily on or off to generate the second current.

11. The current stimulator of claim 1, wherein the capacitor comprises a variable capacitor bank with a ¼ times to 4 times variable capacitance.

12. An operating method of a current stimulator, comprising:

generating a first current injectable into a cranial nerve cell through a current mirroring based on a plurality of transistor pairs comprised in a first current generation circuit;

generating a second current smaller than the first current by controlling a charge rate based on a voltage difference between terminals of a capacitor comprised in a second current generation circuit driven by a clock;

controlling a first output impedance of the first current generation circuit and a second output impedance of the second current generation circuit to have a magnitude greater than or equal to a predetermined ratio to a load impedance corresponding to the cranial nerve cell;

generating currents by overlapping the first current corresponding to the first output impedance and the second current corresponding to the second output impedance; and injecting the generated currents into the cranial nerve cell.

13. The operating method of claim 12, wherein the generating of the second current comprises adjusting a magnitude of the second current by controlling the charge rate based on the voltage difference between the terminals of the capacitor disposed between a first switch and a second switch configured to operate complementarily based on a switching of the clock.

14. The operating method of claim 13, wherein the magnitude of the second current is determined based on any one or any combination of any two or more of a frequency of the clock, a capacitance of the capacitor, and a difference between an input voltage and an output voltage of the second current generation circuit.

15. The operating method of claim 12, wherein the generating of the second current comprises generating the second current in response to a second current section in which the magnitude of the second current increases linearly as a frequency of the clock increases.

16. The operating method of claim 12, wherein the predetermined ratio is a 10 times ratio.

17. The operating method of claim 12, further comprising:

operating in any one of a first operating mode in which the first current is generated and a second operating mode in which the second current is generated, by controlling a negative feedback path and the first switch and the second switch at the terminals of the capacitor comprised in the second current generation circuit.

18. The operating method of claim 17, wherein the operating in any one of the operating modes comprises:

turning off the negative feedback path and applying the clock to the first switch and the second switch to switch the first switch and the second switch at the terminals of the capacitor to an on state to generate a negative first current to be generated; or turning off the negative feedback path and applying, in response to the first operating mode, the clock to the first switch and the second switch to switch the first switch and the second switch at the terminals of the capacitor complementarily on or off to generate a positive first current to be generated.

19. The operating method of claim 17, wherein the operating in any one of the operating modes comprises:

turning on the negative feedback path and applying, in response to the second operating mode, the clock to the first switch and the second switch to switch the first switch and the second switch at the terminals of the capacitor complementarily on or off to generate the second current.

20. A non-transitory computer-readable storage medium storing instructions that, when executed by a processor, cause the processor to perform the method of claim 12.

\* \* \* \* \*